US00PP37799P2

(12) United States Plant Patent
Arts

(10) Patent No.: US PP37,799 P2
(45) Date of Patent: Oct. 20, 2026

(54) HYDRANGEA PLANT NAMED 'H225901'

(50) Latin Name: *Hydrangea macrophylla*
Varietal Denomination: H225901

(71) Applicant: HYDRANGEA BREEDERS ASSOCIATION B.V., De Kwakel (NL)

(72) Inventor: Niels Arts, Aalsmeer (NL)

( * ) Notice: Subject to any disclaimer, the term of this patent is extended or adjusted under 35 U.S.C. 154(b) by 0 days.

(21) Appl. No.: 19/569,866

(22) Filed: Mar. 17, 2026

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

(56) References Cited

U.S. PATENT DOCUMENTS

PP30,452 P2 * 4/2019 Arts ..... A01H 6/48
Plt./250

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Hydrangea* plant named 'H225901', characterized by its compact, upright and uniformly mounded plant habit; vigorous growth habit and rapid growth rate; freely branching habit with strong, thick and sturdy stems; freely and uniformly flowering habit; mophead-type inflorescences with numerous sterile flowers that are purplish red in color; and good postproduction longevity.

2 Drawing Sheets

Figure 1:
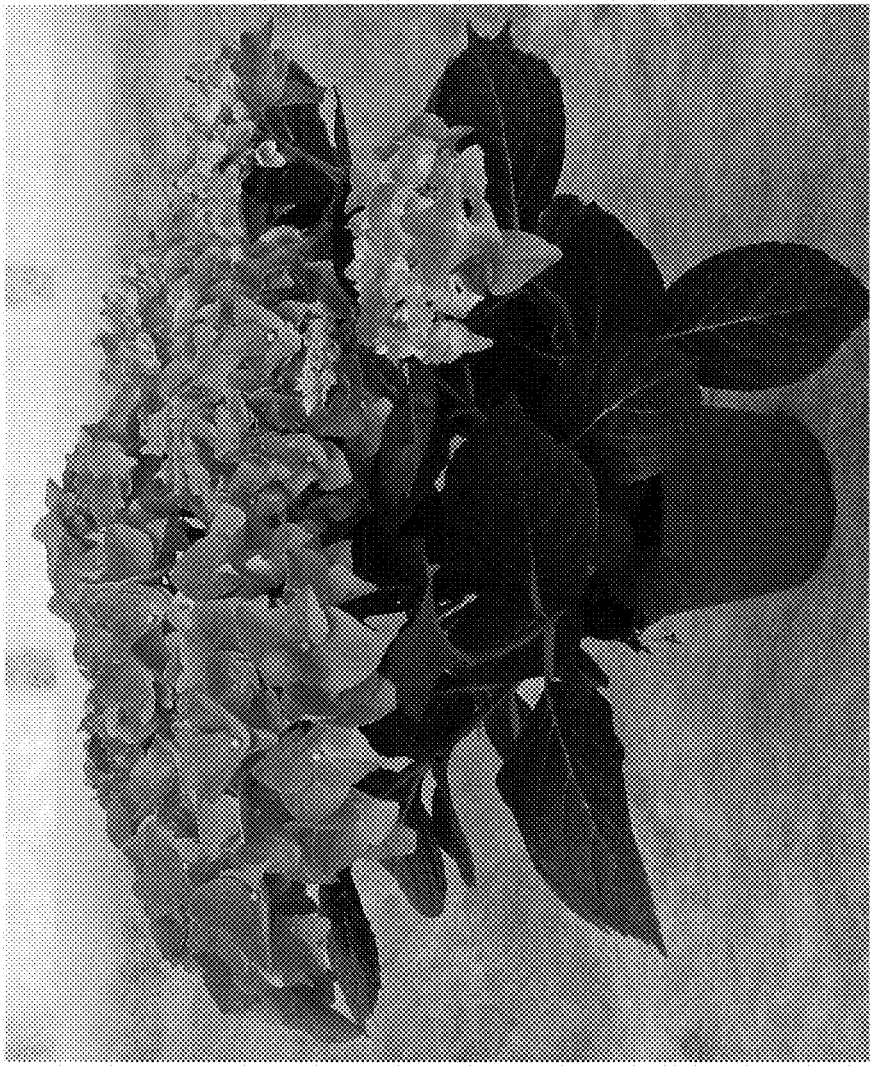

Botanical designation: *Hydrangea macrophylla.*
Cultivar denomination: 'H225901'.

A European Community Plant Breeder's Rights application for the instant plant was filed by the Applicant/Assignee of the instant application, *Hydrangea* Breeders Association B.V. of De Kwakel, The Netherlands on May 13, 2025, application number 2025/1008, and published on Aug. 15, 2025. Foreign priority is not claimed to this application.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H225901'.

The new *Hydrangea* plant is a product of a planned breeding program conducted by the Inventor in De Kwakel, The Netherlands. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor during the summer of 2016 in De Kwakel, The Netherlands, of *Hydrangea macrophylla* 'HBA 202911', not patented, as the female, or seed, parent with *Hydrangea macrophylla* 'H213906', disclosed in U.S. Plant Pat. No. 26,509, as the male, or pollen, parent. The new *Hydrangea* plant was discovered and selected by the Inventor as a single flowering plant from within the progeny of the stated cross-pollination in a controlled greenhouse environment in De Kwakel, The Netherlands during the spring of 2018.

Asexual reproduction of the new *Hydrangea* plant by vegetative tip cuttings in a controlled environment in De Kwakel, The Netherlands since the summer of 2018 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H225901'. These characteristics in combination distinguish 'H225901' as a new and distinct *Hydrangea* plant:

1. Compact, upright and uniformly mounded plant habit.
2. Vigorous growth habit and rapid growth rate.
3. Freely branching habit with strong, thick and sturdy stems.
4. Freely and uniformly flowering habit.
5. Mophead-type inflorescences with numerous sterile flowers that are purplish red in color.
6. Good postproduction longevity.

Plants of the new *Hydrangea* can be compared to plants of the female parent, 'HBA 202911'. Plants of the new *Hydrangea* differ primarily from plants of 'HBA 202911' in sterile flower color as sterile flowers of plants of the new *Hydrangea* are darker purplish red than sterile flowers of plants of 'HBA 202911'.

Plants of the new *Hydrangea* can be compared to plants of the male parent, 'H213906'. Plants of the new *Hydrangea* differ primarily from plants of 'H213906' in plant habit as plants of the new *Hydrangea* are more compact than plants of 'H213906'. In addition, plants of the new *Hydrangea* are more freely branching than plants of 'H213906'.

Plants of the new *Hydrangea* can be compared to plants of the *Hydrangea macrophylla* 'H217905', disclosed in U.S. Plant Pat. No. 30,452. In side-by-side comparisons, plants of the new *Hydrangea* differ primarily from plants of 'H217905' in the following characteristics:

1. Plants of the new *Hydrangea* are more freely branching than plants of 'H217905'.
2. Sterile flowers of plants of the new *Hydrangea* are darker purplish red than sterile flowers of plants of 'H217905'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type.

Colors in the photographs may differ from the color values cited in the detailed botanical description which accurately describe the colors of the new *Hydrangea* plant.

The photograph on the first sheet (FIG. 1) is a side perspective view of a typical flowering plant of 'H225901'.

Figure 2:
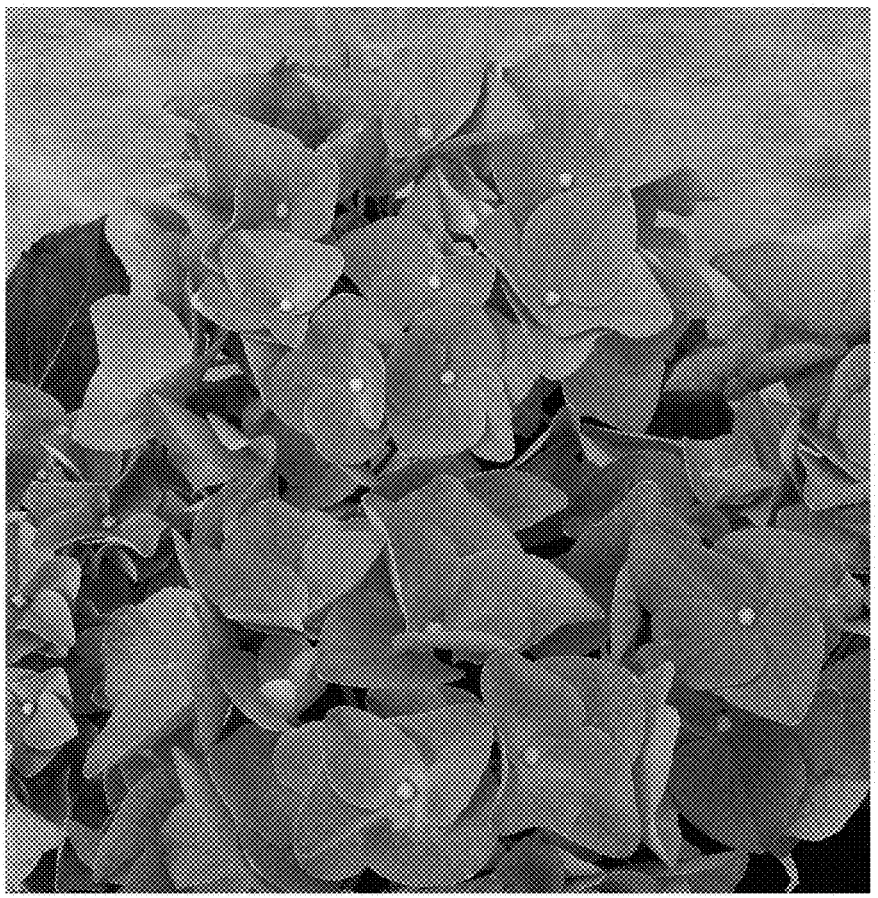

The photograph on the second sheet (FIG. 2) is a close-up view of typical inflorescences of 'H225901'.

DETAILED BOTANICAL DESCRIPTION

Plants used in the aforementioned photographs and in the following detailed description were grown during the late spring and early summer in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were one year old when the photographs and description were taken. Plants of the new *Hydrangea* can be treated with aluminum sulfate to "blue" the inflorescences. In the following description, color references are made to The Royal Horticultural Society Colour Chart, 1995 Edition, except where general terms of ordinary dictionary significance are used.

Botanical description: *Hydrangea macrophylla* 'H225901'.

Parentage:

*Female, or seed, parent.*—*Hydrangea macrophylla* 'HBA 202911', not patented.

*Male, or pollen, parent.*—*Hydrangea macrophylla* 'H213906', disclosed in U.S. Plant Pat. No. 26,509.

Propagation:

*Type cutting.*—By vegetative tip cuttings.

*Time to initiate roots, summer.*—About two weeks at temperatures about 23° C.

*Time to initiate roots, winter.*—About 18 days at temperatures about 20° C.

*Time to produce a rooted young plant, summer.*—About four weeks at temperatures about 23° C.

*Time to produce a rooted young plant, winter.*—About five weeks at temperatures about 20° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, upright and uniformly mounded plant habit; strong and sturdy stems; rapid growth rate and vigorous growth habit.

*Plant height.*—About 25 cm to 35 cm.

*Plant diameter or area of spread.*—About 40 cm.

Lateral branch description:

*Branching habit.*—Freely branching habit; when pinched, about ten lateral branches develop per plant.

*Length.*—About 20 cm to 25 cm.

*Diameter.*—About 6 mm.

*Internode length.*—About 3 cm to 4 cm.

*Texture.*—Smooth, glabrous; fully developed, woody.

*Aspect.*—Upright to about 70° from vertical.

*Strength.*—Sturdy.

*Color.*—Close to 146C; at the nodes, close to 187A; lenticels, close to 187A; if woody, close to 177C.

Leaf description:

*Arrangement.*—Opposite, simple.

*Length.*—About 8 cm to 10 cm.

*Width.*—About 6.5 cm to 7 cm.

*Shape.*—Ovate.

*Apex.*—Acute.

*Base.*—Obtuse.

*Margin.*—Dentate.

*Texture, upper and lower surfaces.*—Smooth to somewhat rugose, glabrous.

*Venation pattern.*—Pinnate.

*Color.*—Developing leaves, upper surface: Close to 139A. Developing leaves, lower surface: Close to 137D. Fully expanded leaves, upper surface: Close to 139B; venation, close to 145B. Fully expanded leaves, lower surface: Close to 137C; venation, close to 145C.

*Petioles.*—Length: About 2 cm. Diameter: About 5 mm. Texture, upper and lower surfaces: Smooth, glabrous. Color, upper and lower surfaces: Close to 145C.

Flower description:

*Flower type and habit.*—Small and inconspicuous fertile flowers and showy sterile flowers arranged on mophead-type terminal panicles; panicles upright and globular in shape; fertile flowers face upright and sterile flowers face upright to outwardly depending on their position in the inflorescence.

*Fragrance.*—None detected.

*Natural time to flowering.*—Plants flower during and throughout the summer in The Netherlands.

*Flower longevity.*—Fertile flowers last about one month on the plant, fertile flowers not persistent; sterile flowers last about four months on the plant, sterile flowers persistent.

*Quantity of flowers.*—Freely flowering habit; about 30 to 50 fertile flowers and about 60 sterile flowers per panicle.

*Panicle height.*—About 8 cm to 10 cm.

*Panicle diameter.*—About 15 cm to 17 cm.

*Fertile flower buds.*—Length: About 3 mm. Diameter: About 3 mm. Shape: Spherical. Color: Close to 145C.

*Sterile flower buds.*—Length: About 3 mm. Diameter: About 3 mm. Shape: Spherical. Color: Close to 145C.

*Fertile flower diameter.*—About 6 mm by 6 mm.

*Fertile flower depth (height).*—About 6 mm.

*Sterile flower diameter.*—About 5 cm by 4.5 cm to 5 cm.

*Sterile flower depth (height).*—About 1 cm.

*Petals, fertile flowers.*—Quantity and arrangement: About five in a single whorl. Length: About 3 mm to 4 mm. Width: About 2 mm. Shape: Ovate. Apex: Acute. Base: Cuneate. Margin: Entire. Texture, upper and lower surfaces: Smooth, glabrous. Color: When opening, upper and lower surfaces: Close to 145C. Fully opened, upper and lower surfaces: Close to 73C; color does not change with subsequent development.

*Petals, sterile flowers.*—Quantity and arrangement: About four in a single whorl. Length: About 4 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 145C. Fully opened, upper and lower surfaces: Close to 58D; color does not change with subsequent development.

*Sepals, fertile flowers.*—Quantity and arrangement: About five in a single whorl. Length: About 2 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 145B. Fully opened, upper and lower surfaces: Close to 145D; color does not change with subsequent development.

*Sepals, sterile flowers.*—Quantity and arrangement: About four in a single whorl. Length: About 2.5 cm. Width: About 2.5 cm. Shape: Deltoid. Apex: Acute to obtuse. Base: Cuneate. Margin: Entire. Texture, upper and lower surfaces: Smooth to slightly rugose, glabrous. Color: When opening, upper and lower surfaces: Close to 144D. Fully opened, upper surface: Close to 63A; color does not change with subsequent development; when "blued" with aluminum sulfate, color becomes closer to 96C. Fully opened, lower surface: Close to 63B; color does not change with subsequent development.

*Pedicels, fertile flowers.*—Length: About 5 mm to 10 mm. Diameter: About 1 mm. Strength: Sturdy. Aspect: Mostly upright. Texture: Smooth, glabrous. Color: Close to 63D.

*Pedicels, sterile flowers.*—Length: About 2.5 cm. Diameter: About 2 mm. Strength: Sturdy. Aspect: About 45° from vertical. Texture: Smooth, glabrous. Color: Close to 58A.

*Reproductive organs, fertile flowers.*—Stamens: Quantity per flower: About eight. Filament length: About 1 mm. Filament color: Close to 69B. Anther length: About 1 mm. Anther shape: Conical. Anther color: Close to 69B. Pollen amount: Abundant. Pollen color: Close to 155D. Pistils: Pistil quantity per flower: One. Pistil length: About 3 mm. Stigma shape: Oval. Stigma color: Close to 69B. Style length: About 1 mm. Style color: Close to 69B. Ovary color: Close to 69C.

*Reproductive organs, sterile flowers.*—Stamens: Quantity per flower: About eight. Filament length: About 2 mm. Filament color: Close to 65B. Anther length: About 1 mm. Anther shape: Conical. Anther color: Close to 65B. Pollen amount: Abundant. Pollen color: Close to 155D. Pistils: Pistil quantity per flower: One. Pistil length: About 3 mm to 4 mm. Stigma shape: Oval. Stigma color: Close to 150D. Style length: About 2 mm to 3 mm. Style color: Close to 150D. Ovary color: Close to 150D.

*Seeds, only produced by fertile flowers.*—Quantity per fertile flower: About 20 to 30. Length: About 0.5 mm. Diameter: About 0.1 mm. Color: Close to 200C.

Pathogen & pest resistance: To date, plants of the new *Hydrangea* grown under commercial production conditions have not been observed to be resistant to pathogens and pests common to *Hydrangea* plants.

Temperature tolerance: Plants of the new *Hydrangea* have been shown to tolerate temperatures ranging from about 3° C. to about 38° C.

It is claimed:

1. A new and distinct *Hydrangea* plant named 'H225901' as herein illustrated and described.

* * * * *